(12) United States Patent
Angel et al.

(10) Patent No.: US 7,005,145 B2
(45) Date of Patent: Feb. 28, 2006

(54) ANTIBACTERIAL AND FUNGICIDAL POLYMER DISPERSIONS AND POLYMER SOLUTIONS

(75) Inventors: Maximilian Angel, Schifferstadt (DE); Bernhard Fussnegger, Kirrweiler (DE); Silke Gebert, Grünstadt (DE)

(73) Assignee: BASF Aktiengesellschaft, Ludwigshafer (DE)

( * ) Notice: Subject to any disclaimer, the term of this patent is extended or adjusted under 35 U.S.C. 154(b) by 21 days.

(21) Appl. No.: 10/467,942

(22) PCT Filed: Feb. 14, 2002

(86) PCT No.: PCT/EP02/01557

§ 371 (c)(1),
(2), (4) Date: Aug. 14, 2003

(87) PCT Pub. No.: WO02/068518

PCT Pub. Date: Sep. 6, 2002

(65) Prior Publication Data
US 2004/0077748 A1    Apr. 22, 2004

(30) Foreign Application Priority Data
Feb. 27, 2001  (DE) .............................. 101 09 447

(51) Int. Cl.
*A01N 59/16*    (2006.01)
*A01N 59/20*    (2006.01)
*C08K 3/08*    (2006.01)

(52) U.S. Cl. ...................... 424/618; 424/617; 424/618; 424/619; 424/630; 424/631; 424/632; 424/633; 424/634; 424/635; 424/637; 424/638; 424/649; 514/495; 514/499; 514/500; 523/122; 205/701

(58) Field of Classification Search ........ 424/617–619, 424/630–635, 637–638, 649; 514/495, 499, 514/500; 523/122; 205/701
See application file for complete search history.

(56) References Cited

U.S. PATENT DOCUMENTS

| 4,291,125 A | 9/1981 | Greatbatch |
| 5,736,591 A | 4/1998 | Dunn |

FOREIGN PATENT DOCUMENTS

| DE | 30 37 046 | 7/1981 |
| DE | 197 07221 | 8/1998 |

*Primary Examiner*—John Pak
(74) *Attorney, Agent, or Firm*—Novak Druce & Quigg

(57) ABSTRACT

The invention relates to polymer dispersions or polymer solutions that are given antibacterial and fungicidal properties by metal ions of group Ib of the Periodic table. According to the invention, a) the polymer dispersions or polymer solutions are not produced using controllers that contain thiol groups, b) the metal ions have been introduced by means of an electrochemical process and c) said dispersions or solutions do not contain any active quantity of organic biocides.

2 Claims, No Drawings

ANTIBACTERIAL AND FUNGICIDAL POLYMER DISPERSIONS AND POLYMER SOLUTIONS

This application is a 371 of PCT/EP02/01557, filed on Feb. 14, 2002.

This invention relates to aqueous polymer dispersions or solutions rendered antibacterial and antifungal by ions of metals of group Ib of the periodic table of the elements, wherein the polymers were prepared without regulators or without thiol regulators and the metal ions were introduced using an electrochemical process.

Polymers and especially aqueous polymer solutions and polymer dispersions are susceptible to becoming infected with bacteria, yeasts or fungi. Such an infection may give rise for example to discolorations of the product and to a change in the viscosity, the pH and the odor. In the case of polymers used for pharmaceutical purposes, moreover, all pharmacopoeias require that certain maximum germ count values be complied with.

Examples of microorganisms which attack polymers are the bacteria *Alcaligenes faecalis, Escherichia coli, Micrococcus flavus, Proteus vulgaris, Pseudomonas aeruginosa, Pseudomonas putida, Pseudomonas stutzeri*, the yeasts *Candida albicans, Rhodotorula albicans, Saccharomyces cerevisiae* and the molds *Aspergillus niger, Aspergillus terreus* and *Geotrichum candidum*.

To protect the polymer solutions and dispersions and also the products produced therefrom against microbial infestation, they have to be preserved, so that product properties remain constant over a defined period and germ count limits are complied with.

A multiplicity of techniques for preserving polymers against bacterial or fungal infection are known. As well as formaldehyde or generally aldehyde generators, a multiplicity of bactericidal substances such as sodium hypochlorite, hydrogen peroxide but also organic chemical bactericides as mentioned in U.S. Pat. No. 5,736,591 for example are used against microbial infection.

DE 197 07 221 A1 also discloses numerous proposals for solving the problem of bacterial, yeast and fungal infection and infection by other microorganisms using antibiotic metal ions, such as silver, copper and zinc.

DE 197 07 221 A1 describes a specific solution in a process for preparing antibacterially and fungicidally active polymer dispersions which contain metal ions. This solution can be used to protect a multiplicity of further polymer dispersions. A particular advantage is said to be that the problem of admixing polymer dispersions with metal ions, especially in the form of metal salts, is solved by the addition of the silver-containing polymer dispersion instead of the addition of the silver salt. This is because polymer dispersions tend to coagulate irreversibly on addition of electrolytes, whether in pure or dissolved form, especially at the point where the drops come into contact with the aqueous polymer dispersion, owing to the local high concentration. It is a distinct disadvantage that the addition of silver-containing polymers to other dispersions, as well as the desired antibacterially and fungicidally active metal ions, will inevitably introduce further components (polymeric protective polymer) into the polymer dispersion to be rendered antibacterial and fungicidal. The introduction of further components having a fundamentally different composition than the polymer to be rendered antibacterial and fungicidal can be considered an appreciable disadvantage for a wide variety of reasons, for example with regard to approval requirements governing polymers for pharmaceutical, cosmetic or other applications for example. Nor is it possible to rule out an adverse effect on the properties of the polymers to be rendered antibacterial and antifungal.

To obtain effective antibacterial and fungicidal protection, therefore, U.S. Pat. No. 5,736,591 proposes using a combination of metals of group Ib and organic biocides. Despite this combination of inorganic and organic biocides, the metal ions have to be used in a concentration of from 1 to 50 ppm. The metal ions are introduced in the form of a salt solution in the examples. However, it is also stated at column 3 lines 37 to 39 that "An electrolytic process for adding Group Ib metals to the latex can also be utilized".

It is an object of the present invention to further lower the required metal ion concentration without the use of organic biocides becoming necessary. This requirement applies particularly to cosmetic and pharmaceutical preparations.

We have found that this object is achieved according to the invention by polymer dispersions or solutions rendered antibacterial and fungicidal by metal ions of group Ib of the periodic table of the elements, characterized by (a) said polymer dispersions or solutions having been prepared without regulators or without thiol regulators, (b) said metal ions having been introduced using an electrochemical process and (c) the absence of effective amounts of organic biocides.

The novel process is advantageous in that it requires less than 1 ppm of metal ions, in many cases less than 0.6 ppm of metal ions. This is particularly important for cosmetic and pharmaceutical preparations where only low metal contents are admissible or desirable.

The invention rests on the surprising discovery that the low levels of metal ions of generally below 1 ppm are sufficient when the dispersions are free of compounds containing thiol groups. It is believed that the latex dispersions of U.S. Pat. No. 5,736,591 were prepared using such regulators containing thiol groups and therefore required higher concentrations of metal ions and additionally organic biocides in order that adequate antibacterial and fungicidal protection was attained.

Useful ions of metals of group Ib of the periodic table of the elements include especially copper and in particular silver.

Useful polymer dispersions or solutions to be stabilized according to the invention include polymer dispersions or solutions containing any, small amounts or predominantly water as a dispersion medium and solution medium respectively, with the proviso that they have not been prepared using regulators or using regulators which contain no thiol groups.

The polymer contains in general not less than 40% by weight, particularly preferably not less than 60% by weight, most preferably not less than 80% by weight, of units derived from principal monomers, so called.

Principal monomers are selected from $C_1$–$C_{20}$-alkyl (meth)acrylates, vinyl esters of carboxylic acids containing up to 20 carbon atoms, styrenics of up to 20 carbon atoms, ethylenically unsaturated nitriles, vinyl halides, vinyl ethers of alcohols containing 1 to 10 carbon atoms, aliphatic hydrocarbons containing 2 to 8 carbon atoms and 1 or 2 double bonds or mixtures thereof.

Useful dispersions and solutions to be stabilized according to the invention include in particular those which have a pH of from 4.5 to 9 and contain unsaturated esters as principal monomers, such as vinyl.esters and especially acrylic esters.

Especially alkyl (meth)acrylates containing a $C_1$–$C_{10}$-alkyl radical are suitable, such as methyl methacrylate, methyl acrylate, n-butyl acrylate, ethyl acrylate and 2-ethylhexyl acrylate.

Mixtures of alkyl (meth)acrylates are also suitable.

Useful vinyl esters of carboxylic acids containing 1 to 20 carbon atoms include for example vinyl laurate, vinyl stearate, vinyl propionate, vinyl versatate and vinyl acetate.

Useful styrenic compounds include vinyltoluene, o-methylstyrene, p-methylstyrene, o-butylstyrene, 4-n-butylstyrene, 4-n-decylstyrene and preferably styrene. Examples of nitriles are acrylonitrile and methacrylonitrile.

Vinyl halides are chlorine-, fluorine- or bromine-substituted ethylenically unsaturated compounds, preferably vinyl chloride and vinylidene chloride.

Useful vinyl ethers include for example vinyl methyl ether or vinyl isobutyl ether. Preference is given to vinyl ethers of alcohols containing 1 to 4 carbon atoms.

Useful hydrocarbons containing 2 to 8 carbon atoms and two olefinic double bonds include butadiene, isoprene and chloroprene and useful hydrocarbons containing 2 to 8 carbon atoms and one double bond include for example ethylene or propylene.

Preferred principal monomers are $C_1$–$C_{10}$-alkyl acrylates and methacrylates, especially $C_1$–$C_8$-alkyl acrylates and methacrylates and vinyl esters, especially vinyl acetate, and mixtures thereof.

Very particular preference is given to methyl acrylate, methyl methacrylate, ethyl acrylate and vinyl acetate and also mixtures thereof.

As well as units derived from principal monomers, the free-radically polymerized polymer can contain units derived from further monomers, for example monomers having carboxylic acid, sulfonic acid or phosphonic acid groups. Carboxylic acid groups are preferred. Acrylic acid, methacrylic acid, itaconic acid, maleic acid and fumaric acid are suitable for example. Preference is given to methacrylic acid and acrylic acid.

Useful further monomers also include for example hydroxyl-containing monomers, especially $C_1$–$C_{10}$-hydroxyalkyl (meth)acrylates, but also (meth)acrylamide.

Useful further monomers further include phenyloxyethyl glycol mono(meth)acrylate, glycidyl acrylate, glycidyl methacrylate, amino(meth)acrylates such as 2-aminoethyl (meth)acrylate.

Useful further monomers also include crosslinking monomers and also monomers having hydrolyzable silicon groups.

In a preferred embodiment, the polymers are prepared by emulsion polymerization and the polymers are therefore emulsion polymers.

However, they can also be prepared by solution polymerization in water, mixed aqueous/nonaqueous solvents or nonaqueous solvents and subsequent dispersion in water.

An emulsion polymerization utilizes ionic and/or nonionic emulsifiers and/or protective colloids, such as polyvinylpyrrolidone or polyvinyl alcohol, or stabilizers as surface-active compounds.

A detailed description of suitable protective colloids is given in Houben-Weyl, Methoden der organischen Chemie, volume XIV/1, Makromolekulare Stoffe, Georg-Thieme-Verlag, Stuttgart, 1961, pp. 411–420. Suitable emulsifiers include anionic, cationic and nonionic emulsifiers. As accompanying surface-active substances it is preferred to use exclusively emulsifiers, whose molecular weights—unlike those of the protective colloids—are usually below 2,000 g/mol. Where mixtures of surface-active substances are used the individual components must of course be mutually compatible, which in case of doubt can be checked using a few preliminary experiments. Anionic and nonionic emulsifiers are preferably used as surface-active substances. Examples of customary accompanying emulsifiers are ethoxylated fatty alcohols (EO degree: 3 to 50, alkyl radical: $C_8$ to $C_{36}$), ethoxylated mono-, di- and tri-alkylphenols (EO degree: 3 to 50, alkyl radical: $C_4$ to $C_9$), alkali metal salts of dialkyl esters of sulfosuccinic acid, and alkali metal salts and ammonium salts of alkyl sulfates (alkyl radical: $C_8$ to $C_{12}$), of ethoxylated alkanols (EO degree: 4 to 30, alkyl radical: $C_{12}$ to $C_{18}$), of ethoxylated alkylphenols (EO degree: 3 to 100, alkyl radical: $C_4$ to $C_9$), of alkylsulfonic acids (alkyl radical: $C_{12}$ to $C_{18}$) and of alkylarylsulfonic acids (alkyl radical: $C_9$ to $C_{18}$).

Further suitable emulsifiers are compounds of the formula II

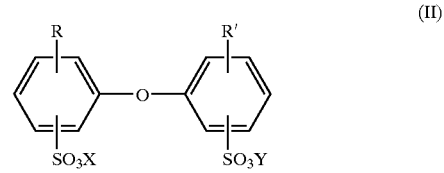

in which R and R' are hydrogen or $C_4$–$C_{14}$-alkyl but are not both hydrogen, and X and Y can be alkali metal ions and/or ammonium ions. R and R' are preferably linear or branched alkyl radicals having 6 to 18 carbons, or hydrogen, and in particular have 6, 12 or 16 carbons, and are not both simultaneously hydrogen. X and Y are preferably sodium, potassium or ammonium ions, sodium being particularly preferred. Particularly advantageous compounds II are those in which X and Y are sodium, R is branched $C_{12}$-alkyl and R' is hydrogen or R. In many cases use is made of technical-grade mixtures containing a proportion of from 50 to 90% by weight of the monoalkylated product, an example being Dowfax®2A1 (trademark of Dow Chemical Company).

Suitable emulsifiers are also given in Houben-Weyl, Methoden der organischen Chemie, volume 14/1, Makromolekulare Stoffe, Georg Thieme Verlag, Stuttgart, 1961, pages 192 to 208.

Examples of commercial emulsifiers are Dowfax®2 A1, Emulan®NP 50, Dextrol® OC 50, Emulgator 825, Emulgator 825 S, Emulan® OG, Texapon® NSO, Nekanil® 904 S, Lumiten® I-RA, Lumiten E 3065, Disponil FES 77, Lutensol AT 18, Steinapol VSL, Emulphor NPS 25.

The surface-active substance is normally used in amounts of from 0.1 to 10% by weight, based on the monomers that are to be polymerized.

Examples of water-soluble initiators for the emulsion polymerization are ammonium salts and alkali metal salts of peroxodisulfuric acid, e.g. sodium peroxodisulfate, hydrogen peroxide or organic peroxides, e.g. tert-butyl hydroperoxide.

Reduction-oxidation (redox) initiator systems are also suitable, consisting of at least one, usually inorganic reducing agent and of an inorganic or organic oxidizing agent.

The oxidation component comprises, for example, the abovementioned initiators for emulsion polymerization.

The reduction component comprises for example ascorbic acid. The redox initiator systems can be used along with soluble metal compounds whose metallic component is able to exist in a plurality of valency states.

Customary redox initiator systems include for example ascorbic acid/iron(II) sulfate together with sodium peroxodisulfate or hydrogen peroxide. The individual components, for example the reduction component, may also be mixtures.

The abovementioned compounds are mostly employed in the form of aqueous solutions, the lower concentration being determined by the amount of water which is acceptable in the dispersion and the upper concentration by the solubility of the relevant compound in water. In general the concentration is from 0.1 to 30% by weight, preferably from 0.5 to 20% by weight, particularly preferably from 1.0 to 10% by weight, based on the solution.

The amount of initiators is generally from 0.1 to 10% by weight, preferably from 0.5 to 5% by weight, based on the monomers that are to be polymerized. It is also possible to use a plurality of different initiators in the course of the emulsion polymerization.

The polymerization can utilize regulators, for example in amounts from 0 to 5% by weight, based on the monomers to be polymerized, preferably from 0 to 0.8% by weight. Useful regulators are mentioned for example in DE-A 197 12 247 at page 4. However, no regulator may be used which contains a thiol group, such as tert-butyl mercaptan, ethylhexyl thioglycolate, mercaptoethanol, mercaptopropyltrimethoxysilane or tert-dodecyl mercaptan.

The emulsion polymerization of the polymers to be rendered antibacterial and fungicidal is generally conducted at from 30 to 130° C., preferably from 50 to 90° C. The polymerization medium can consist either just of water or of mixtures of water and water-miscible liquids such as methanol. Preferably, only water is used. The emulsion polymerization can be carried out either batchwise or in the form of a feed process, including a stepwise or gradient procedure. Preference is given to the feed process, in which some of the polymerization batch is introduced as initial charge, heated to the polymerization temperature and then initially polymerized, and then the remainder of the polymerization batch is supplied, in the course of continuing polymerization, to the polymerization zone continuously, stepwise or under a concentration gradient and usually by way of a plurality of spatially separate feed streams, of which one or more contain the monomers in pure or emulsified form.

The manner in which the initiator is added to the polymerization vessel in the course of the free-radical aqueous emulsion polymerization is familiar to the person of average skill in the art. It can either be included entirely in the initial charge to the polymerization vessel or else introduced stepwise or continuously in the course of the free-radical aqueous emulsion polymerization at the rate at which it is consumed. In an individual case this will depend, as familiar to the person of average skill in the art, both on the chemical nature of the initiator system and on the polymerization temperature. Preferably, some is included in the initial charge and the remainder is supplied to the polymerization zone at the rate at which it is consumed.

In order to remove the residual monomers it is common to add initiator even after the end of the actual emulsion polymerization, i.e. after a monomer conversion of at least 95%.

In the case of the feed process the individual components can be supplied to the reactor from above, laterally or from below, through the reactor base.

The emulsion polymerization produces aqueous polymer dispersions with, in general, solids contents of from 15 to 75% by weight, preferably from 30 to 50% by weight.

The glass transition temperature of the polymeric binder or of the emulsion polymer is preferably in the range from −60 to +100° C., particularly preferably in the range from −20 to +60° C. and very particularly preferably in the range from −10 to +50° C.

The glass transition temperature can be determined by customary methods such as differential thermal analysis or differential scanning calorimetry (see for example ASTM 3418/82, "midpoint temperature").

The polymers are thus prepared from dispersions or solutions and can contain for example from 25 to 85% of water as a dispersion or solution medium respectively.

The dispersions or solutions preferably contain from 50 to 70% by weight of water.

The metal ions, preferably silver ions, are introduced into the dispersions or solutions using an electrochemical process. This is accomplished using conventional apparatus where a current flows between silver electrodes and the aqueous substrate to be silverized serves as an electrolyte when passing between the electrodes.

There are basically 2 alternatives for the silverization. Either (a) the water to be used later for the polymerization is silverized in advance in the desired concentration or preferably (b) the silver ions are introduced into the ready-produced polymer.

In case (b), the entirety of the conditions (current strength, electrode surface area, flow rate) is chosen so that the average local concentration of the silver ions in the volume element between the electrodes does not exceed 5 ppm, preferably 2 ppm. To attain the desired final concentration without local concentration exceedence, it can be advantageous to pass the silverized dispersions and solutions again or repeatedly through the apparatus. But it is also possible to treat only part of the dispersion stream and then to mix this treated part stream in with the untreated stream.

Useful apparatus includes for example Elektro-Katadyn apparatus from Katadyn® (Wallisellen, Switzerland).

EXAMPLES a) Preparation of Polymers

Polymer 1

A solution of 500 g of completely ion-free water, 3.5 g of sodium laurylsulfate and 50 g of feed 1 is heated to 80° C. and then admixed with 7.5 g of sodium peroxodisulfate (7% strength in water) and thereafter continuously with feeds 1 and 2 at 80° C. in the course of 2 hours.

| Feed 1 |
| --- |
| 500 g of completely ion-free water |
| 23 g of ethoxylated nonylphenol (100 EO units) |
| 7 g of sodium laurylsulfate (15% strength in water) |
| 370 g of ethyl acrylate |
| 160 g of methyl methacrylate |

| Feed 2 |
| --- |
| 21 g of sodium peroxodisulfate (2.5% strength in water) |

This is followed by 2 h of supplementary polymerization, cooling to room temperature and admixing in succession with a solution of 0.2 g of hydrogen peroxide (30% strength) in 9 g of completely ion-free water and with a solution of 0.3 g of ascorbic acid and 0.5 g of iron(II) sulfate (1% strength in water) in 24 g of completely ion-free water. The pH is then adjusted to a value of 7.5 by addition of sodium pyrophosphate (3% strength in water) and sodium hydroxide (10% strength in water).

Polymer 2

The procedure for polymer 1 is repeated, with the proviso that feed 1 contains 10 g of isopropanol as a regulator.

b) Methods of Introducing the Silver b1) Direct Electrochemical Introduction of Silver into the Dispersions The dispersion to be admixed with silver ions is flowed through an apparatus consisting of the type EK4 Electro-Katadyn silverizer from Katadyn Produkte AG CH-8304 Wallisellen and a pump. To be able to obtain the desired silver dose, the flow rate of the pump has to be determined. The silverizing current to be set is computed from the flow rate and the desired silver dose. This is done using Faraday's formula.

$1 \text{ A} \stackrel{\wedge}{=} 4 \text{ g of Ag}^+ \text{ per hour}$
$1 \text{ mA} \stackrel{\wedge}{=} 4 \text{ mg of Ag}^+ \text{ per hour}$ Illustrative computation:

| | |
|---|---|
| Flow rate | 2 m$^3$/h |
| Desired silver dose (Ag) | 0.2 ppm (0.2 mg/l) |
| Silver for 2 m$^3$ of dispersion as per Example 1 | 400 mg |
| 1 mA $\stackrel{\wedge}{=}$ 4 mg of Ag$^+$/h | |
| Silverizing current (400:4 = 100) | 100 mA |

The computed silverizing current is set and the pump is used to pass the dispersion of Example 1 through the Electro-Katadyn EK-4 unit. As soon as the product is pumped through the Electro-Katadyn unit, the silverizing current is switched on and the dispersion is admixed with the desired amount of silver. The dispersion of polymer 1 was admixed with 0.2, 0.5 and 1 ppm of silver.

Dispersion 2 was treated similarly.

b2) Introducing the Silver Into the Water Used for Preparing the Dispersion

The preparation of polymer 1 is repeated, except that 1 ppm of silver ions was introduced by the electrochemical process described under (c) into the completely ion-free water used.

c) Test Method 20 g of each of polymers 1 and 2 were inoculated with 0.2 ml of the individual germ suspensions (*Escherichia coli, Pseudomonas aeriginosa, Staphylococcus aurens, Candida albicans, Aspergillus niger*) and homogenized, so that an inoculum of from 1.8 to 3.4×10$^5$ germs was present.

The germ count was determined at once, after 14 days and after 28 days. The results are shown below in Tables 1 to 7.

TABLE 1

| Dispersion corresponding to polymer 1 with 0.2 ppm of silver | Recovery rate | Germ count/g of sample in batch after | | | |
|---|---|---|---|---|---|
| | | inoculum | at once | 14 days | 28 days |
| *Escherichia coli* ATCC 8739 | 91% | 2.0 × 10$^5$ | 1.8 × 10$^5$ | <10 | <10 |
| *Pseudomonas aeruginosa* ATCC 9027 | 86% | 3.4 × 10$^5$ | 1.3 × 10$^5$ | <10 | <10 |
| *Staphylococcus aureus* ATCC 6538 | 94% | 1.8 × 10$^5$ | 1.5 × 10$^5$ | <10 | <10 |
| *Candida albicans* ATCC 10231 | 93% | 3.2 × 10$^5$ | 2.0 × 10$^5$ | <10 | <10 |
| *Aspergillus niger* ATCC 16404 | 97% | 2.5 × 10$^5$ | 1.4 × 10$^5$ | <10 | <10 |

Evaluation:

According to the result of the microbiological investigation conducted, the effectiveness of the preservation meets the Ph. Eur. 3, 2000 requirements for oral use preparations.

TABLE 2

| Dispersion corresponding to polymer 2 with 0.5 ppm of silver | Recovery rate | Germ count/g of sample in batch after | | | |
|---|---|---|---|---|---|
| | | inoculum | at once | 14 days | 28 days |
| *Escherichia coli* ATCC 8739 | 88% | 2.0 × 10$^5$ | 6.6 × 10$^4$ | <10 | <10 |
| *Pseudomonas aeruginosa* ATCC 9027 | 91% | 3.4 × 10$^5$ | 8.6 × 10$^4$ | <10 | <10 |
| *Staphylococcus aureus* ATCC 6538 | 94% | 1.8 × 10$^5$ | 6.3 × 10$^4$ | <10 | <10 |
| *Candida albicans* ATCC 10231 | 94% | 3.2 × 10$^5$ | 1.1 × 10$^5$ | <10 | <10 |
| *Aspergillus niger* ATCC 16404 | 92% | 2.5 × 10$^5$ | 1.1 × 10$^5$ | <10 | <10 |

Evaluation:

According to the result of the microbiological investigation conducted, the effectiveness of the preservation meets the Ph. Eur. 3, 2000 requirements for oral use preparations.

A repetitive inoculation with 5 different test germs, i.e., a reinoculation after germ death, produced the following results for the dispersion of polymer 1, containing 0.5 ppm of silver, by the use of the test method described under c):

TABLE 3

| 1st inoculation | Recovery rate | Germ count/g of sample in batch after | | | |
|---|---|---|---|---|---|
| | | inoculum | at once | 14 days | 28 days |
| *Escherichia coli* ATCC 8739 | 88% | 2.0 × 10$^5$ | 6.6 × 10$^4$ | <10 | <10 |
| *Pseudomonas aeruginosa* ATCC 9027 | 91% | 3.4 × 10$^5$ | 8.6 × 10$^4$ | <10 | <10 |
| *Staphylococcus aureus* ATCC 6538 | 94% | 1.8 × 10$^5$ | 6.3 × 10$^4$ | <10 | <10 |

TABLE 3-continued

| 1st inoculation | Recovery rate | Germ count/g of sample in batch after | | |
|---|---|---|---|---|
| | | inoculum | at once | 14 days | 28 days |
| Candida albicans ATCC 10231 | 94% | $3.2 \times 10^5$ | $1.1 \times 10^5$ | <10 | <10 |
| Aspergillus niger ATCC 16404 | 92% | $2.5 \times 10^5$ | $1.1 \times 10^5$ | <10 | <10 |

Evaluation:
According to the result of the microbiological investigation conducted, the effectiveness of the preservation meets the Ph. Eur. 3, 2000 requirements for oral use preparations.

TABLE 4

| 2nd inoculation (after 28 days) | Germ count/g of sample in batch after | | |
|---|---|---|---|
| | inoculum | 14 days | 28 days |
| Escherichia coli ATCC 8739 | $2.6 \times 10^5$ | n.a. | <10 |
| Pseudomonas aeruginosa ATCC 9027 | $3.5 \times 10^5$ | <10 | <10 |
| Staphylococcus aureus ATCC 6538 | $3.2 \times 10^5$ | <10 | <10 |
| Candida albicans ATCC 10231 | $4.2 \times 10^5$ | <10 | <10 |
| Aspergillus niger ATCC 16404 | $2.1 \times 10^5$ | <10 | <10 |

Evaluation:
According to the result of the microbiological investigation conducted, the effectiveness of the preservation after the 2nd challenge is sufficient.
n.a.=not assessable

TABLE 5

| 3rd inoculation (after 56 days) | Germ count/g of sample in batch after | | |
|---|---|---|---|
| | inoculum | 14 days | 28 days |
| Escherichia coli ATCC 8739 | $3.1 \times 10^5$ | <10 | <10 |
| Pseudomonas aeruginosa ATCC 9027 | $3.2 \times 10^5$ | <10 | <10 |
| Staphylococcus aureus ATCC 6538 | $1.9 \times 10^5$ | <10 | <10 |
| Candida albicans ATCC 10231 | $1.3 \times 10^5$ | <10 | <10 |
| Aspergillus niger ATCC 16404 | $2.2 \times 10^5$ | <10 | <10 |

Evaluation:
According to the result of the microbiological investigation conducted, the effectiveness of the preservation after the 3rd challenge is sufficient.

TABLE 6

| 4th inoculation (after 3 months) | Germ count/g of sample in batch after | | |
|---|---|---|---|
| | inoculum | 14 days | 28 days |
| Escherichia coli ATCC 8739 | $3.2 \times 10^5$ | <10 | <10 |
| Pseudomonas aeruginosa ATCC 9027 | $2.4 \times 10^5$ | <10 | <10 |
| Staphylococcus aureus ATCC 6538 | $3.0 \times 10^5$ | <10 | <10 |

TABLE 6-continued

| 4th inoculation (after 3 months) | Germ count/g of sample in batch after | | |
|---|---|---|---|
| | inoculum | 14 days | 28 days |
| Candida albicans ATCC 10231 | $4.1 \times 10^5$ | <10 | <10 |
| Aspergillus niger ATCC 16404 | $2.7 \times 10^5$ | <10 | <10 |

Evaluation:
According to the result of the microbiological investigation conducted, the effectiveness of the preservation after the 4th challenge is sufficient.

TABLE 7

| 5th inoculation (after 5 months) | Germ count/g of sample in batch after | | |
|---|---|---|---|
| | inoculum | 14 days | 28 days |
| Escherichia coli ATCC 8739 | $3.6 \times 10^5$ | <10 | <10 |
| Pseudomonas aeruginosa ATCC 9027 | $3.4 \times 10^5$ | <10 | <10 |
| Staphylococcus aureus ATCC 6538 | $7.6 \times 10^5$ | <10 | <10 |
| Candida albicans ATCC 10231 | $3.6 \times 10^5$ | <10 | <10 |
| Aspergillus niger ATCC 16404 | $3.6 \times 10^5$ | <10 | <10 |

Evaluation:
According to the result of the microbiological investigation conducted, the effectiveness of the preservation after the 5th challenge is sufficient.

d) Production of Preparations

Granules for Matrix Tablets

Dispersion 2, having a polymer content of 30% and a silver content of 0.4 ppm, is used as a granulation fluid in a fluidized bed granulator to produce granules for matrix tablets. The use for this purpose takes place without further dilution or formulation.

Production of Granules

A fluidized bed granulator (for example a Glatt WSG 15 apparatus) is initially charged with 3.5 kg of paracetamol powder as active material and also 1.7 kg of lactose monohydrate as filler and the initial charge is granulated by spraying with 5.67 liters of the abovementioned dispersion. This is followed by drying to a residual moisture content of <2%.

The following spraying and drying conditions were set:

| Spray type | Top spray | |
|---|---|---|
| Air inlet temperature | ° C. | 55 |
| Air inlet humidity | % | 7 |
| Air exit temperature | ° C. | 28–30 |
| Air exit humidity | % | 73–76 |
| Nozzle opening | mm | 1.5 |
| Spray rate | g/min | ca. 60 |
| Spray pressure | bar | 2.1 |
| Drying | min | 5 |
| Residual moisture | % | 1.6 |

The granules obtained are free flowing and pressable into matrix tablets under the conditions customary in the art.

Tablet Coating

Dispersion 1, having a silver content of 0.2 ppm of silver, was used to prepare the following formulation for coating tablet cores and applied by spraying.

Composition of Spray Formulation

|  | Use level [g] | Composition [% solids] |
|---|---|---|
| Dispersion 1 with 0.2 ppm of silver | 1757 | 70.8 |
| Triacetin | 55 | 7.4 |
| Talc | 122 | 16.4 |
| Titanium dioxide | 20 | 2.7 |
| Kollidon 30 | 20 | 2.7 |
| Water | 1440 | |
| Sum total | 3420 | 100 |

Preparation of Spray Formulation

Triacetin is first dissolved in 1100 g of water. The dispersion is gradually added and the mixture homogenized by constant stirring.

Separately, the Kollidon® 30 ingredient is dissolved in 340 g of water and then this solution is admixed with titanium dioxide and talc and subsequently treated using a homogenizer, for example an Ultraturrax. The pigment suspension obtained is finally stirred into the dispersion with plasticizer and sprayed onto tablet cores under the conditions mentioned hereinbelow:

| | |
|---|---|
| Coating machine | Hüttlin HKC 5 TJ Coater |
| Loading | 3.2 kg |
| Air inlet temperature | 62° C. |
| Air outlet temperature | 34° C. |
| Product temperature | 37° C. |
| Air rate | 350 m³/h |
| Spray pressure | 0.9 bar |
| Application rate | 4.5 mg/cm² |
| Spray time | 75 min |
| Afterdrying conditions | 42° C./5 min |

The white tablet coating obtained is absolutely uniform after drying and has no cracks or other defects whatever.

We claim:

1. A process for producing polymer dispersions or solutions rendered antibacterial and fungicidal by metal ions of Group Ib of the Periodic Table of the elements, characterized by
   a) preparing polymer dispersions or solutions by polymerizing monomers in the absence of a regulator that contains a thiol group, and
   b) introducing to the polymer dispersions or solutions said metal ions via an electrochemical process;
   wherein there is an absence of effective amounts of organic biocides in said polymer dispersions or solutions, and said polymer dispersions or solutions are further characterized by a metal ion content of less than 0.6 ppm.

2. A process for producing polymer dispersions or solutions rendered antibacterial and fungicidal by metal ions of Group Ib of the Periodic Table of the elements, characterized by
   a) providing water to be used for polymerization, wherein metal ions of Group Ib of the Periodic Table of the elements are introduced to said water via an electrochemical process, and
   b) preparing polymer dispersions or solutions by polymerizing monomers in the water obtained from step (a), in the absence of a regulator that contains a thiol group; wherein there is an absence of effective amounts of organic biocides in said polymer dispersions or solutions, and said polymer dispersions or solutions are further characterized by a metal ion content of less than 0.6 ppm.

* * * * *